(12) United States Patent
Tano et al.

(10) Patent No.: US 6,346,100 B1
(45) Date of Patent: Feb. 12, 2002

(54) LASER TREATMENT APPARATUS AND LASER TREATMENT INFORMATION DISPLAY DEVICE

(75) Inventors: Yasuo Tano, Kobe; Yasuo Ota, Gamagori; Hitoshi Abe, Okazaki, all of (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/318,253

(22) Filed: May 25, 1999

(30) Foreign Application Priority Data

May 29, 1998 (JP) ............................................. 10-148911

(51) Int. Cl.$^7$ ............................................... A61B 18/18
(52) U.S. Cl. ................................ 606/10; 606/4; 606/13; 606/17
(58) Field of Search ...................... 606/3, 4, 5, 10, 606/17, 18, 13; 706/45; 600/308

(56) References Cited

U.S. PATENT DOCUMENTS

| | | | | |
|---|---|---|---|---|
| 4,750,829 A | * | 6/1988 | Wise .......................... 351/160 R |
| 4,839,822 A | * | 6/1989 | Dormond et al. ............... 706/45 |
| 5,098,426 A | * | 3/1992 | Sklar et al. ..................... 606/5 |
| 5,171,242 A | * | 12/1992 | Dewey et al. ................... 606/4 |
| 5,599,340 A | * | 2/1997 | Simon et al. .................... 606/4 |
| 5,661,816 A | * | 8/1997 | Fantone et al. ............... 382/100 |
| 5,666,565 A | * | 9/1997 | Wakabayshi et al. ............ 396/79 |
| 5,823,949 A | * | 10/1998 | Goltra ............................. 600/300 |
| 5,843,070 A | * | 12/1998 | Cambier et al. .................. 606/5 |
| 5,865,829 A | * | 2/1999 | Kitajima .......................... 606/3 |
| 6,099,522 A | * | 8/2000 | Knopp et al. ................... 606/10 |

FOREIGN PATENT DOCUMENTS

| | | |
|---|---|---|
| EP | 0 492 778 A1 | 10/1991 |
| EP | 0 608 052 A2 | 1/1994 |
| EP | 0 697 611 A2 | 6/1995 |
| GB | 2 252 249 A | 8/1992 |
| JP | 8-294507 | 11/1996 |
| JP | 2895014 | 8/1998 |
| WO | WO 92/01430 | 2/1992 |
| WO | WO 93/16631 | 9/1993 |

* cited by examiner

*Primary Examiner*—Roy Gibson
(74) *Attorney, Agent, or Firm*—Finnegan, Henderson, Farabow, Garrett & Dunner, L.L.P.

(57) ABSTRACT

In a treatment laser apparatus, when the data on a laser spot magnification of a contact lens CL to be used for treatment of a patient's eye E is input by means of a controller 7 and the data on a spot size of treatment laser beams in air is input by means of a change knob 4, a real spot size of the laser beams which is irradiated to an affected part of the patient's eye E is calculated in a control section 30 based on the both inputted data, and the calculated result is displayed on a display section 20.

13 Claims, 9 Drawing Sheets

FIG. 6

DIABETIC MACULAR EDEMA

SPOT SIZE : 50~200 μm
PHOTOCOAGULATION TIME : 0.1 sec
LASER OUTPUT : 100 mW
CONTACT LENS : Goldmann
ANESTHESIA : LOCAL ANESTHESIA

FIG. 9
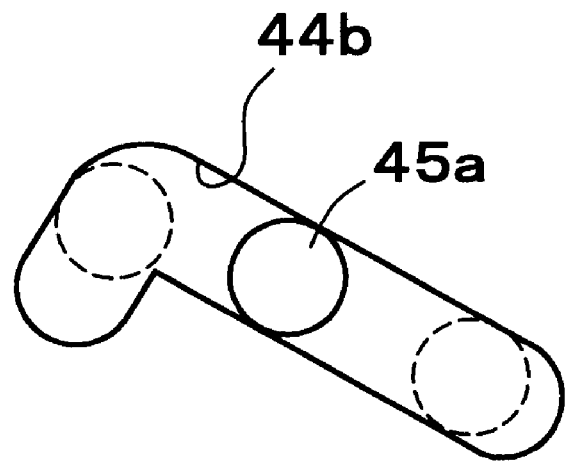
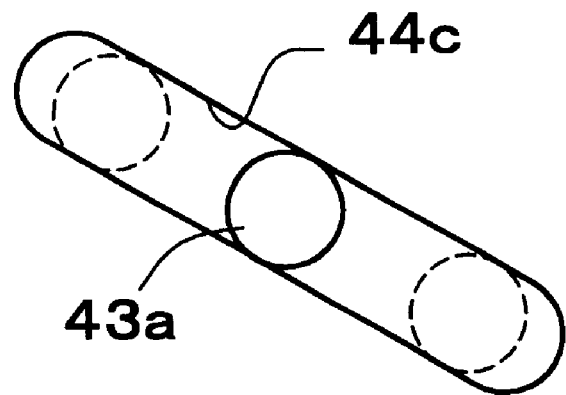

LASER TREATMENT APPARATUS AND LASER TREATMENT INFORMATION DISPLAY DEVICE

BACKGROUND OF THE INVENTION

1. Field of the Invention

The present invention relates to a laser treatment apparatus for irradiating an affected part with treatment laser beams to perform treatment and a laser treatment information display device.

2. Description of Related Art

It has been known that a laser treatment apparatus irradiates an affected part of the patient's eye and its periphery including a macular disease (maculopathy) or a fundus disease such as retinal detachment with treatment laser beams (hereinafter, referred to as laser beams), and performs treatment through photocoagulation or the like.

In photocoagulation treatment for a fundus disease, after setting laser irradiation conditions such as laser output or spot size and the like, an affected part is irradiated with laser beams via a contact lens for retinal photocoagulation.

However, the spot size to be set by the laser treatment apparatus indicates a size at a focal position in air, which is different from a spot size of laser beams with which a fundus affected part is actually irradiated via a contact lens for coagulation. Therefore, an operator determines the spot size suitable to treatment purposes while calculating the actual spot size based on magnification of the contact lens, which is complicated. In addition, there has been danger of incorrect calculation or failure to calculate the spot size.

In addition to a contact lens type, it is necessary to properly set laser irradiation conditions such as laser beam output, spot size, irradiation time and the like according to disease cases. However, these condition settings require experience, and it is difficult for an operator himself to memorize information on the detailed laser irradiation conditions for a variety of disease cases. It is also cumbersome that the operator refers to a document describing information on the laser irradiation conditions every treatment.

SUMMARY OF THE INVENTION

The present invention has been made in view of the above circumstances and has an object to overcome the above problems and to provide a laser treatment apparatus which makes it possible to easily provide information on an actual spot size according to a contact lens to be used.

It is another object of the present invention to provide a laser treatment apparatus which makes it possible to easily provide information on the laser irradiation conditions suitable to a variety of disease cases.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser treatment apparatus for irradiating an affected part with treatment laser beams emitted by a laser source and treating the part, the apparatus including a first input device for inputting data concerning a laser spot magnification of a contact lens to be used for treatment, a second input device for inputting a spot size of the laser beams in air, a calculation device for obtaining a real spot size of the laser beams on the affected part based on the inputted data by the first and second input device, and a spot size display device for displaying a calculation result by the calculation device.

According to another aspect of the present invention, there is provided a laser treatment information display device for displaying information concerning laser treatment for irradiating and treating an affected part with treatment laser beams, the device including a disease case data memory capable of storing a plurality of types of disease cases and data concerning laser beam irradiation conditions corresponding to each disease case, a disease case selector for selecting a disease case to be treated from among the disease case types stored in the disease case data memory, and an irradiation condition display device for displaying data concerning the irradiation conditions corresponding to the disease case selected by the disease case selector.

According to another aspect of the present invention, there is provided a laser treatment information display device for displaying information concerning laser treatment for irradiating and treating an affected part with treatment laser beams, the device including a lens data memory capable of storing a plurality of types of contact lenses to be used for treatment and data concerning laser spot magnifications of each contact lens, a lens selector for selecting a desired contact lens from among the contact lens types stored in the lens data memory, an input device for inputting data in which spot size of the laser beams in air is set in a laser treatment apparatus used for laser treatment, a calculation device for obtaining a real spot size of the laser beams on the affected part based on data concerning the laser spot magnification of the selected contact lens by the lens selector and the inputted data by the input device, and a spot size display device for displaying calculation results of the calculation device.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings,

FIG. 6 is another example displayed on the liquid crystal display part;

FIG. 9 is a partial view of a rotary mount with grooved cams in the lens moving mechanism.

DETAILED DESCRIPTION OF THE PREFERRED EMBODIMENTS

A detailed description of a preferred embodiment of a laser treatment apparatus embodying the present invention will now be given referring to the accompanying drawings.

Figure 1:
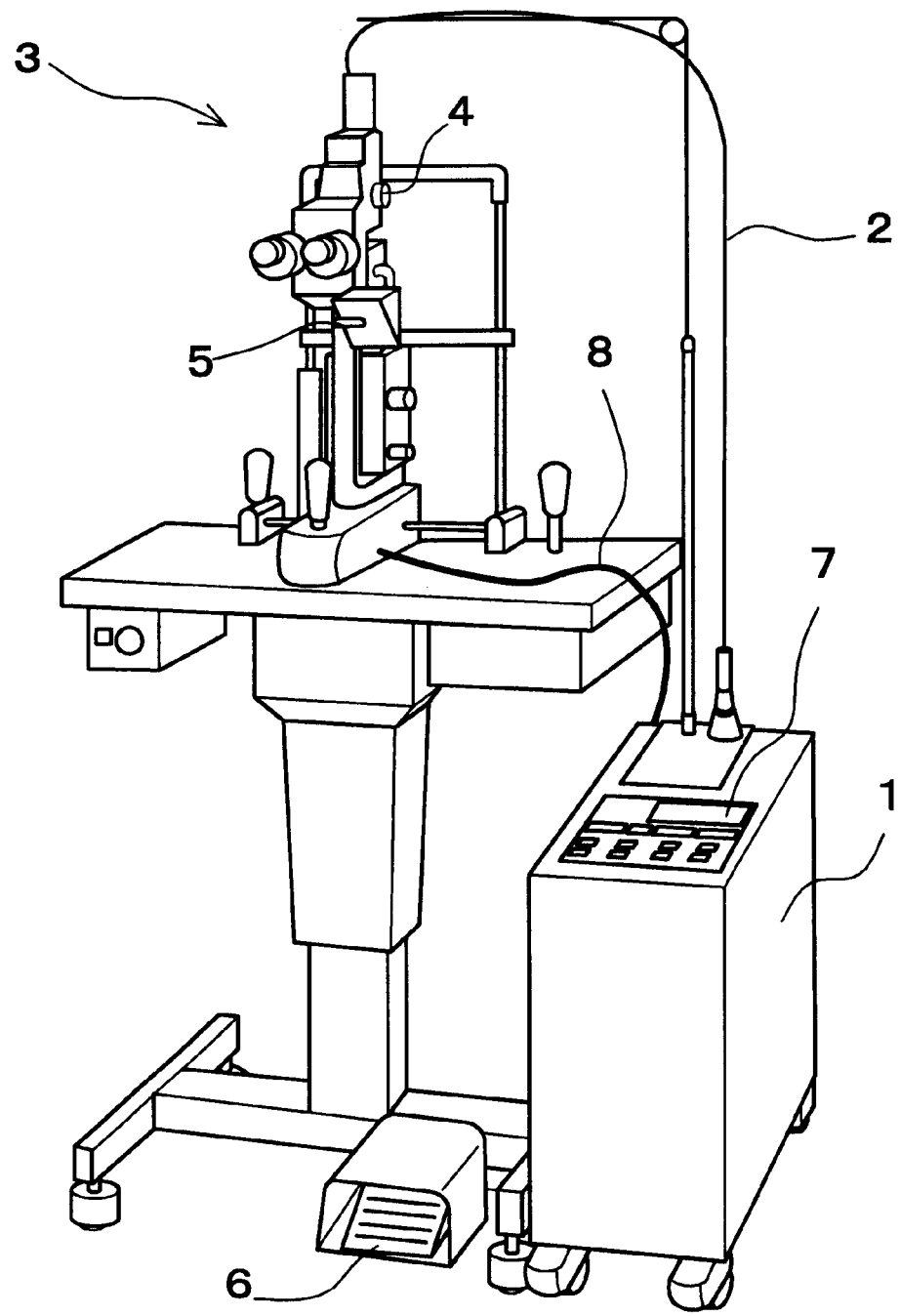
FIG. 1 is an external schematic perspective view of a laser treatment apparatus in an embodiment according to the present invention.
Figure 2:
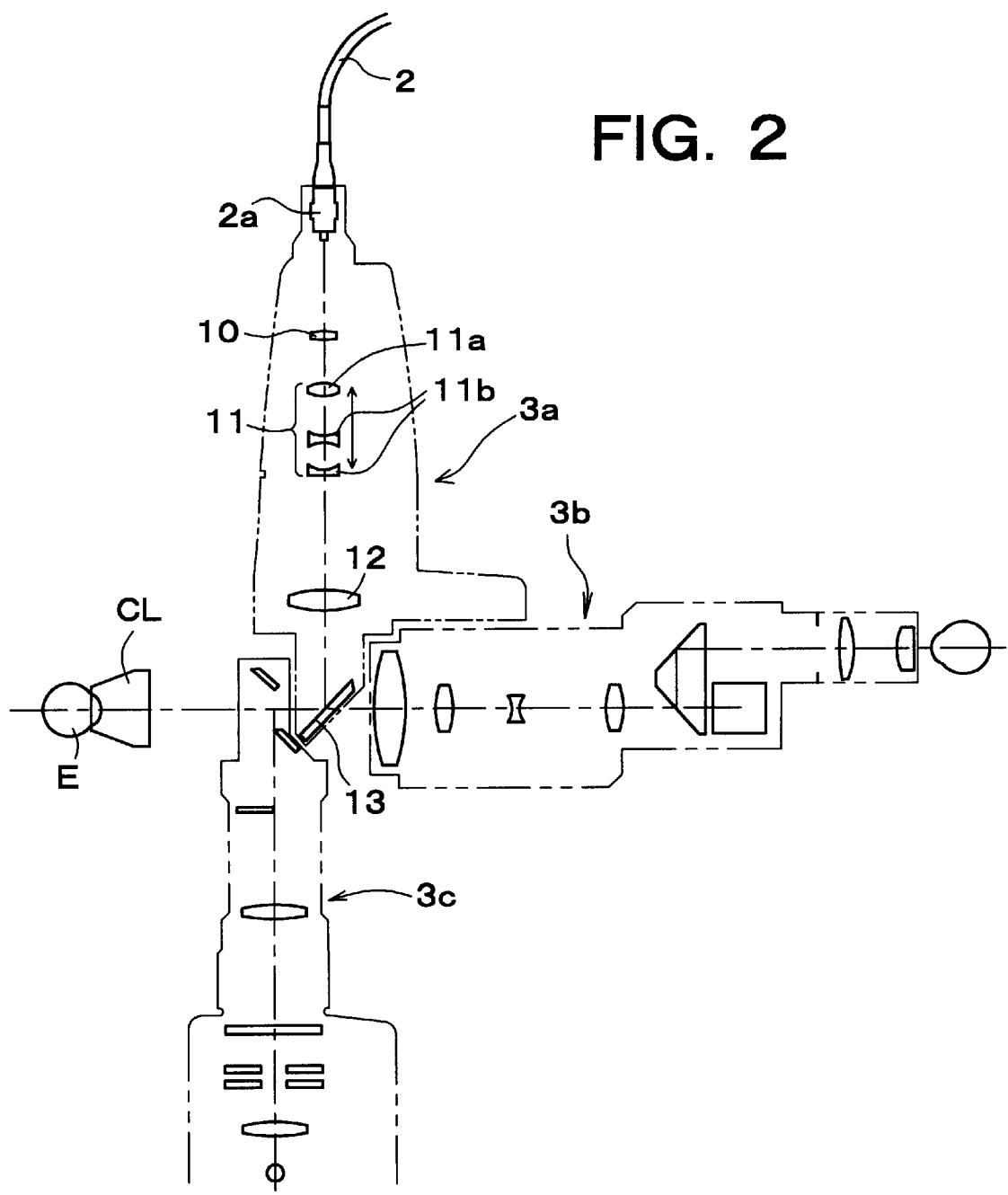
FIG. 2 is a structural view of essential portions of an optical system of the laser treatment apparatus in the present embodiment.
Figure 3:
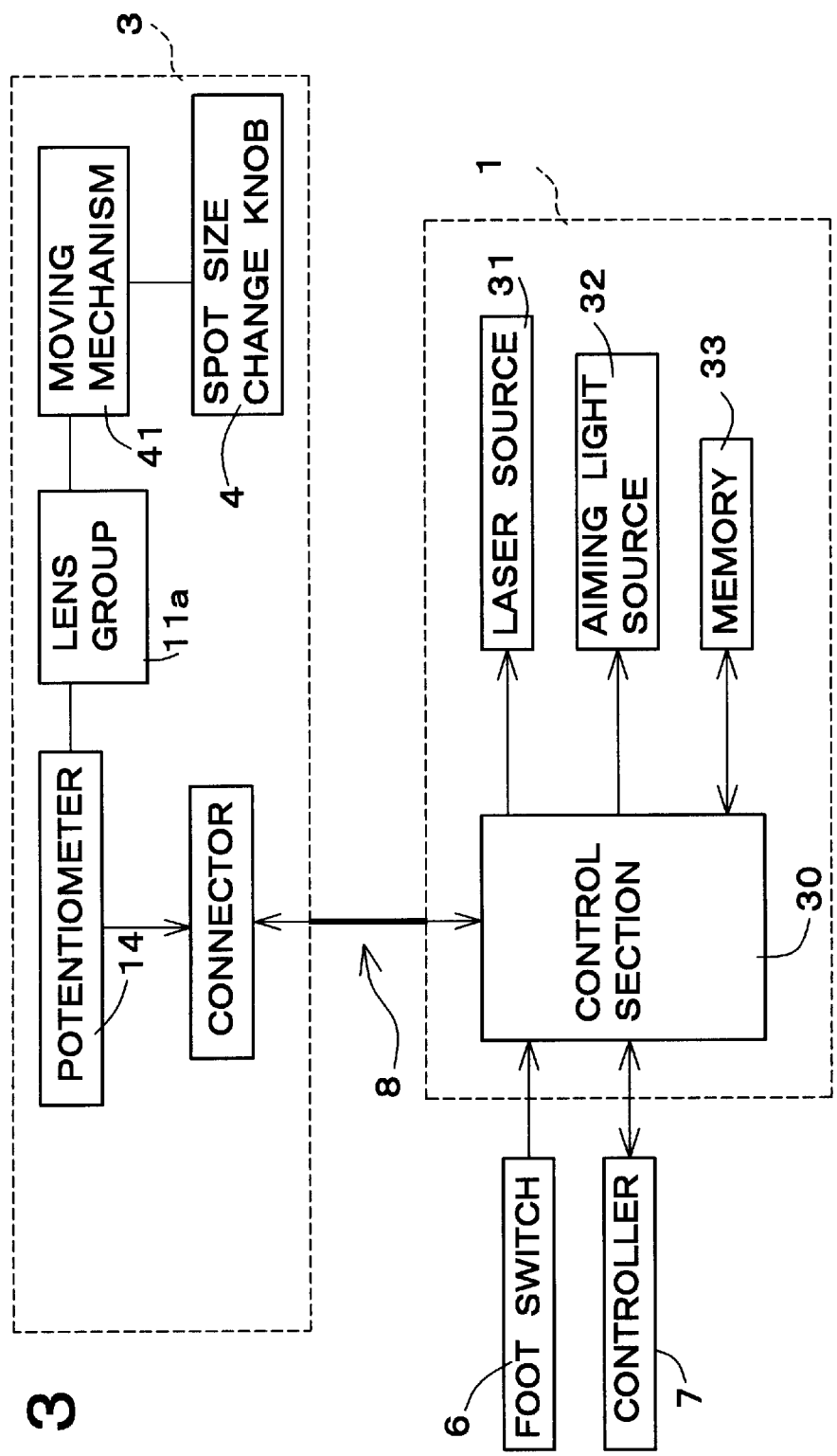
FIG. 3 is a block diagram of essential portions of a control system of the laser treatment apparatus in the present embodiment.

FIG. 1 is an external schematic view of a laser treatment apparatus in this embodiment. FIG. 2 is a structural view of essential portions of an optical system in the laser treatment apparatus. FIG. 3 is a block diagram of essential portions of a control system.

An apparatus main body 1 holds therein a laser source 31, an aiming light source 32, a light delivery system, and a control section 30 and others. An optical fiber 2 delivers treatment laser beams (hereinafter referred to as laser beams) emitted by the laser source 31 and an aiming light emitted by the aiming light source 32 to an irradiation optical system 3a of a slit lamp delivery 3. The slit lamp delivery 3 is provided with the irradiation optical system 3a for delivering laser beams to an affected part of the patient's eye E, a binocular observation optical system 3B for observing the patient's eye E by a variety of optical systems, and an illumination optical system 3c for slit-illuminating the patient's eye E.

The irradiation optical system 3a is constructed of a fixed lens group 10, a variable magnification lens group 11 for changing a spot size, an objective lens group 12, and a driving mirror 13. The variable magnification lens group 11 is constructed of a lens 11a and a pair of lenses 11b. By turning a spot size change knob 4, the lenses 11a and 11b of the magnification lens group 11 moves on an optical axis, and the spot size of the laser beams at a part to be treated is adjusted. The driving mirror 13 is driven by a manipulator 5, thus moving a spot irradiation position.

Figure 8:
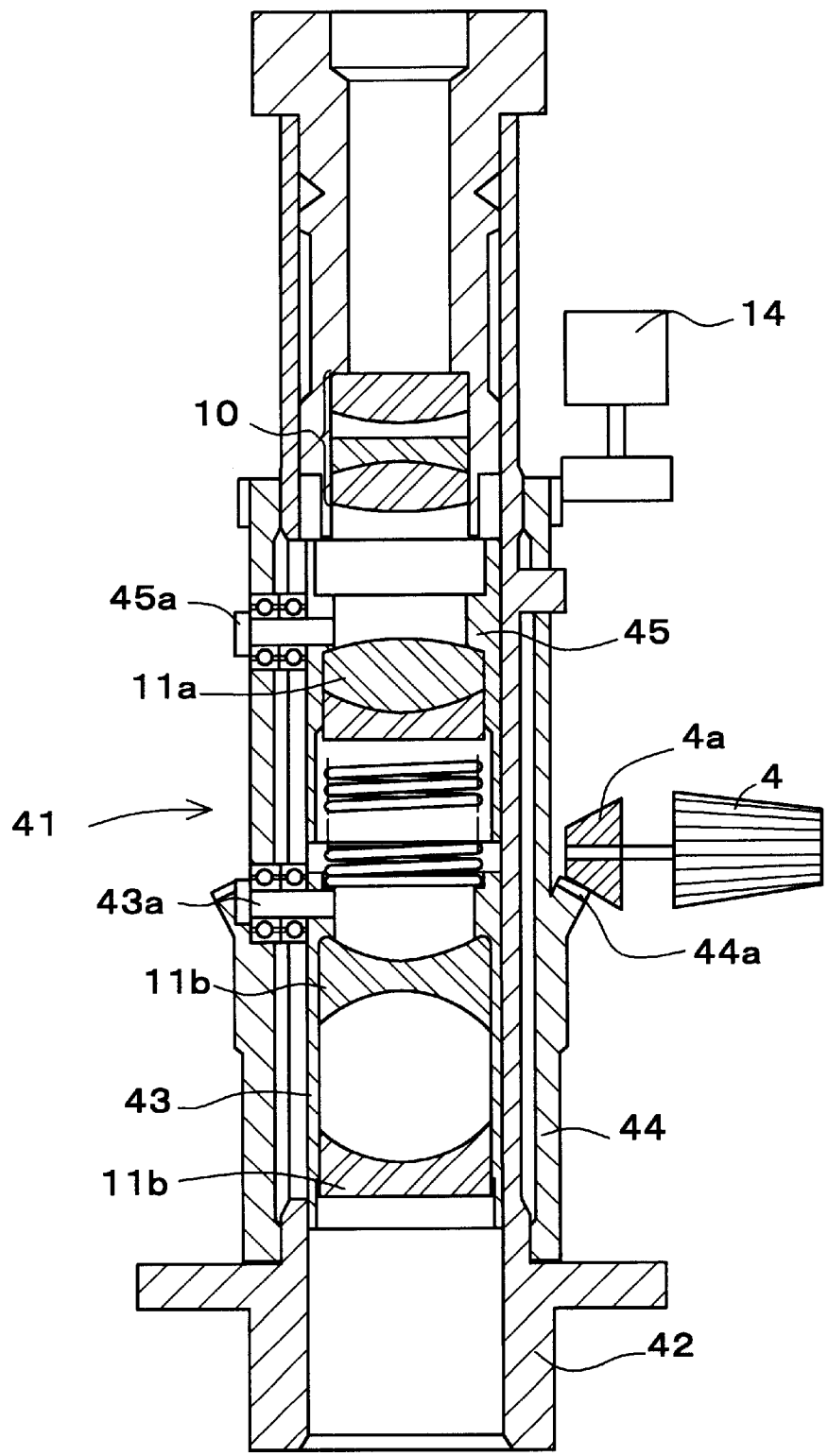
FIG. 8 is a cross sectional view of a lens moving mechanism for moving a variable magnification lens group in the laser treatment apparatus.

FIG. 8 is a cross sectional view of a lens moving mechanism 41 for moving the variable magnification lens group 11. This lens moving mechanism 41 is provided with a hollow fixed mount 42 fixedly mounted in the main body 1 by screws. The fixed lens group 10 constructed of three lenses is secured in the fixed mount 42 at its upper part.

In the fixed mount 42, a second movable mount 43 for fixedly supporting the pair of lenses 11b is held movably in the optical axis direction. A first movable mount 45 for fixedly supporting the lens 11a is also held movably in the optical axis direction above the second movable mount 43.

On the other hand, a rotary mount 44 is rotatably mounted on the outer periphery of the fixed mount 42. The rotary mount 44 is provided with a gear 44a on the outer periphery. In the main body 1, a potentiometer 14 is provided to detect a rotational angle of the rotary mount 44 as a movement quantity of lens group 11.

The rotary mount 44 is provided with grooved cams 44b and 44c as shown in FIG. 9. In the grooved cam 44b, a cam follower 45a attached to the first movable mount 45 is engaged. In the grooved cam 44c, a cam follower 43a attached to the second movable mount 43 is engaged.

Well known observation and illumination optical systems 3b and 3c are used in the present embodiment. A detailed description of these systems is omitted here because there is little relationship with the present invention.

Returning to FIG. 3, a foot switch 6 generates a trigger signal for laser irradiation when an operator depresses. A controller 7 has a variety of switches for setting laser irradiation conditions and a display section for displaying a variety of information for laser irradiation. A control section 30 to be connected to the controller 7 controls the devices such as the light source 31 and others according to the settings of the controller 7. A cable 8 is provided between the slit lamp delivery 3 and the main body 1. This cable 8 serves to transmit spot size change information and an instruction signal by a change knob 4.

Figure 4:
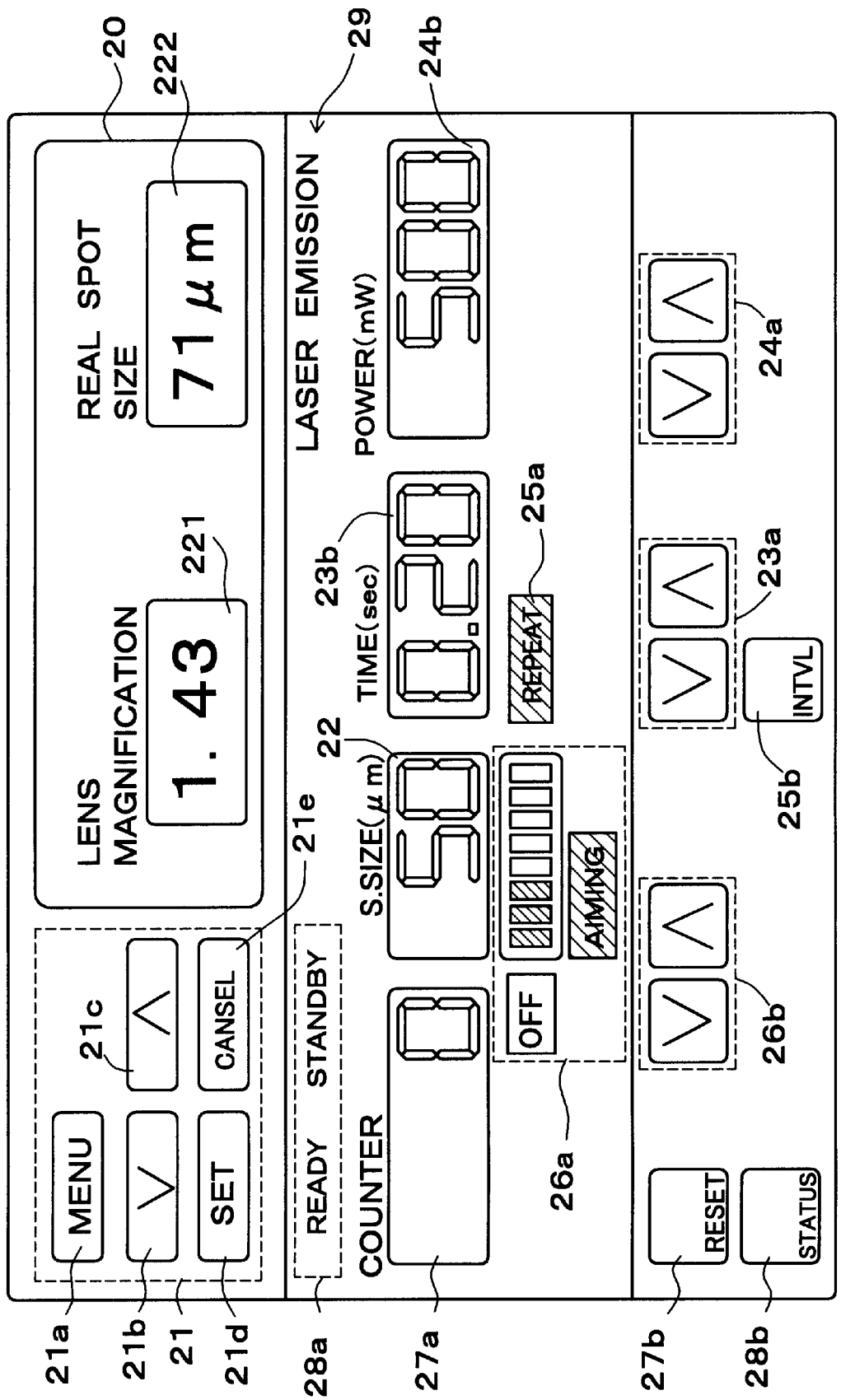
FIG. 4 is a plan view of a controller of the laser treatment apparatus.

FIG. 4 is a plan view of the controller 7. Reference numeral 20 denotes a liquid crystal display section for displaying a variety of data associated with a contact lens used for laser treatment or a disease case. Reference numeral 21 denotes a selection item setting switch group for determining and canceling a selection item displayed on the display section 20.

Reference numeral 22 denotes a display section for displaying a spot size. A value is displayed on this display section 22 when a movement quantity of the lens group 11 moved by the change knob 4 is detected by the potentiometer 14 and is converted as the size at a focal position in air by means of the control section 30.

Reference numeral 23a denotes a switch for setting a laser irradiation (coagulation) time, which is displayed on a display section 23b. Reference numeral 24a denotes a switch for setting laser output, which is displayed on a display section 24b.

In addition, the controller 7 is provided with a REPEAT lamp 25a for displaying repeating irradiation, an INTVL switch 25b for setting ON or OFF of the repeating irradiation or setting the pause time of the repeating irradiation, an aiming light illumination level display section 26a, a switch 26b for setting the illumination level of the aiming light, a counter 27 for counting the count of laser irradiation, a reset switch 27b for resetting the count, a display section 28a for indicating a READY state (laser irradiation enable state) and a STANDBY state (laser irradiation standby state), a STATUS switch 28b for switching the state, and a display section 29 which always lights while power is supplied (during operation) or the like.

Next, operation of the laser treatment apparatus constructed as above is described below.

Figure 5:
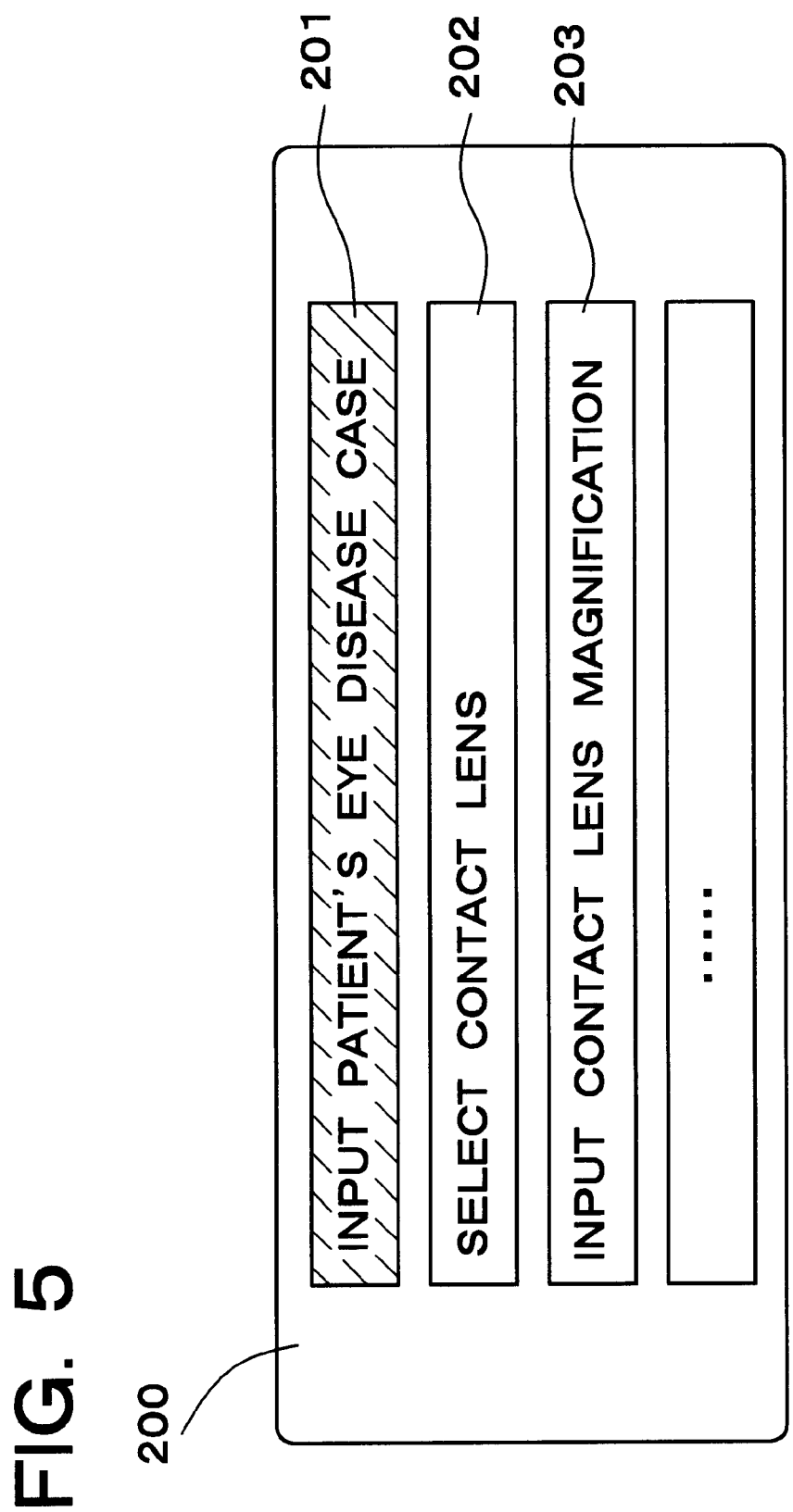
FIG. 5 is an example displayed on a liquid crystal display part of the controller.

Prior to a laser treatment operation, laser irradiation conditions are set by means of the controller 7. At this time, when a MENU switch 21a is pressed if information on the laser irradiation conditions for a disease case of the patient's eye E or information concerning a contact lens to be used for treatment operation is required. On the display section 20, a menu item selection screen 200 as shown in FIG. 5 is displayed, and the selection items are displayed in reverse video. A menu item is selected by operating switches 21b and 21c and moving the reversed display. When a selected item is determined, the next menu can be advanced by pressing a SET switch 21d, and then desired information can be displayed by repeated operation. The immediately preceding menu can be returned by pressing a CANCEL switch 21e, and the first menu screen can be returned by using the MENU switch 21a.

A variety of information in the menu items is stored in a memory 33, the control section 30 retrieves corresponding information based on a switch signal from the controller 7, and the information is displayed on the display section 20.

For example, when an item 201 "Input patient's eye disease case" is selected, a variety of disease cases (for example, retinal breaks (retinal detachment) or diabetic retinopathy and the like) subjected to photocoagulation laser treatment is displayed as a listed menu. Further, when a disease case targeted for treatment is selected from this list menu, the information on laser irradiation conditions, contact lens or the like suitable to that disease case is displayed. FIG. 6 is a display example thereof, on which spot size, irradiation power (laser output), coagulation time, contact lens type, and information concerning anesthesia are displayed. By referring to the thus displayed information, even if the operator does not keep detailed laser irradiation conditions for each disease case in mind, the condition settings for performing adequate treatment can be easily conducted. More detailed irradiation conditions may be set by allowing input of a variety of data such as patient's age, position of the affect part or the like.

Figure 7:
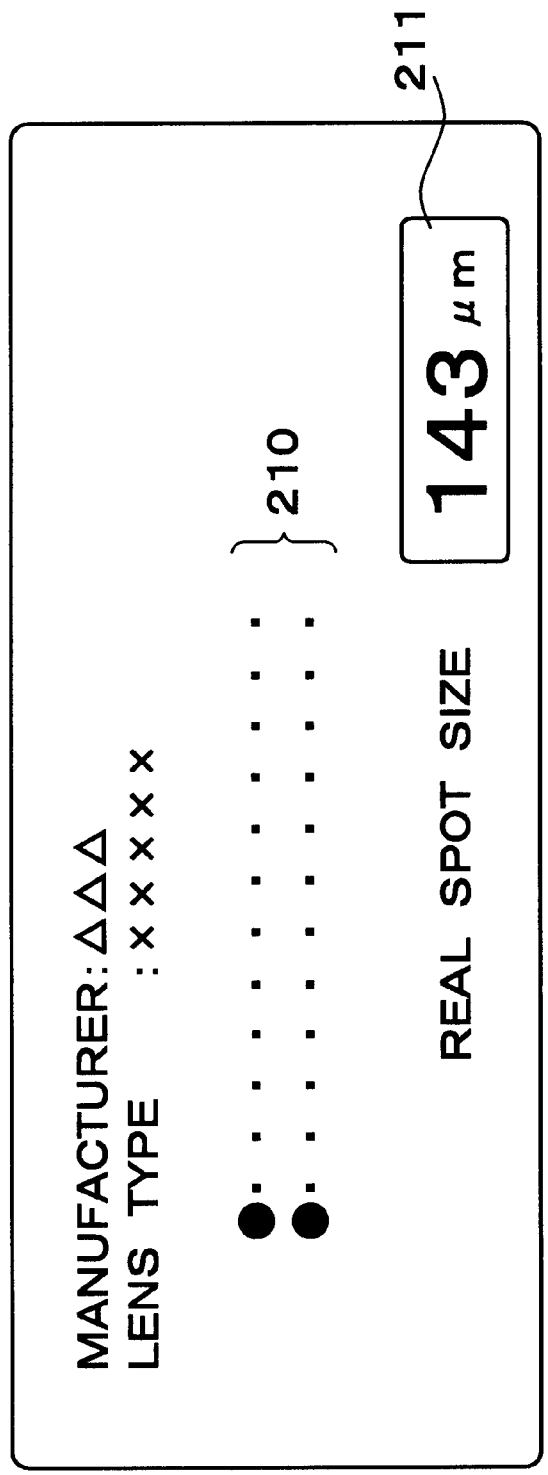
FIG. 7 is another example displayed on the liquid crystal display part.

When an item 202 "Select contact lens" is selected, a contact lens manufacturers list menu is displayed. When a manufacturer of the contact lens to be used for the laser treatment operation is selected from this menu, a list menu indicating the types of contact lenses supplied by the selected manufacturer is then displayed. After the selection of the contact lens type for the laser treatment from the displayed list menu, the information such as contact lens power, magnification, features or the like is displayed on a display field 210 as shown in an example of the screen of FIG. 7. At a display field 211 below the screen, the calculation result concerning the real spot size in the fundus of the patient's eye E is displayed. This real spot size is calculated by the control section 30 based on the spot size data set by the change knob 4 and the selected contact lens magnification data (stored in advance in the memory 33).

In addition, the real irradiation size (spot size) which varies depending on the contact lens used for treatment can be confirmed by inputting contact lens magnification instead of being calculated from the manufacturer's name or type. In this case, an item 203 "Input contact lens magnification" from the menu screen 200 is selected. When this item is selected, as shown in an example of the screen displayed on the display section 20 in FIG. 4, the magnification of the contact lens to be used can be directly inputted. The contact lens magnification can be inputted by increasing or decreasing the value for magnification of the display field 221 by means of the switches 21b and 21c. Based on the inputted magnification value and the data of the spot size set by the change knob 4, the control section 30 calculates the real spot size, and the calculation result is displayed on a display field 222.

Thus, the operator can easily recognize the actual irradiation size without performing cumbersome calculation, and can perform the treatment operation on the patient's eye smoothly. Of course, if spot size is changed by the change knob 4, the value for the spot size displayed on the display section 20 is changed accordingly.

Specifically, when the change knob 4 is turned, the rotary mount 44 is rotated with respect to the fixed mount 42. This rotational angle of the rotary mount 44 is detected by the potentiometer 14. As the rotary mount 44 is rotated, the cam follower 45a tracks the grooved cam 44b, causing the first movable mount 45 to move on the optical axis by a quantity corresponding to the inclination of the grooved cam 44b. The lens 11a is then moved by a predetermined quantity. Simultaneously, the cam follower 43a tracks the grooved cam 44c, causing the second movable mount 43 to move on the optical axis by a quantity corresponding to the inclination of the grooved cam 44c. The lens 11b is then moved by a predetermined quantity. Thus, the lenses 11a and 11b are moved by a predetermined quantity respectively, thereby changing the spot size.

As described above, when the operator successfully obtains treatment information in advance, the operator performs necessary settings such as laser irradiation conditions by means of the controller 7 with reference to the information. When necessary preparation for the apparatus is completed, a selected contact lens CL is brought into contact with the patient's eye E. While observing the patient's eye E through the observation optical system 3c, the operator operates the apparatus to adjust the aiming light to the affected part of the patient's eye E. Upon completion of the aiming light adjustment, the operator depresses the foot switch 6. In response to a signal from the foot switch 6, the laser beams are emitted from the laser source 31 in accordance with the conditions set by means of the controller 7. Then, the laser beams delivered in the optical fiber 2 is emitted from an emitting end 2a thereof, and is irradiated to the affected part of the patient's eye E via the irradiation optical system 3a and the contact lens CL.

As explained above in detail, the laser treatment apparatus in the present embodiment makes it possible for the operator to easily know the information on the real spot size which varies depending on a contact lens to be used in the treatment operation, and to easily set the laser irradiation conditions adequate for various disease cases. Thus, the operator can smoothly carry out the laser treatment with the laser treatment apparatus.

The present invention may be embodied in other specific forms without departing from the spirit or essential characteristics thereof. For instance, in the foregoing description, the operator performs a switch operation and condition settings by referring to the information on the laser irradiation conditions displayed by inputting the disease case. If an attempt is made so as to automatically set the laser irradiation conditions displayed when the disease case is inputted, the input operation can be more simplified.

In addition, the information on laser irradiation conditions or the like displayed in response to the disease case input can be stored so that the data concerning a variety of disease cases is suitable to the operator by providing an input device making it possible for the operator to arbitrarily change and newly add information so that the inputted data is stored in a memory.

If the laser treatment apparatus is provided with an input device for allowing an operator to arbitrarily change the information on laser irradiation conditions displayed when the disease case is selected or to add new cases, and the changed or added data is stored in the memory, the data on various disease cases can be accumulated successively in response to the operator's needs.

In the above embodiment, although description is made on the fundus disease, the laser treatment apparatus according to the invention can be applied to other treatment employed for a contact lens, for example, laser iridotomy or laser trabeculoplasty (LTP) similarly.

In the above embodiment, although a laser treatment apparatus for emitting a single wavelength is described, in the case of a multiple wavelength type laser treatment apparatus such as Ar/Kr (Argon/Krypton), Ar/Dye (Argon/Dye), MW/Kr (Multi-wave/Krypton) lasers, an optimal wavelength for the disease case may be displayed together.

Data concerning the disease cases and contact lens may be displayed and stored by an external apparatus (personal computer or the like) independent of the laser apparatus main body in a manner that the data is transferred to the laser apparatus main body.

Furthermore, a variety of information including the patient information such as disease case displayed on the display section 20, selected contact lens information, irradiation conditions displayed, actual irradiation conditions (laser output value, spot size, irradiation time, and irradiation count), etc. can be printed out through a printer, and stored. This information can be printed out, and also can be stored in an external storage medium such as floppy disk.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A laser treatment apparatus for irradiating an affected part with a treatment laser beam, the apparatus comprising:
    a laser source for emitting the treatment laser beam:
    an irradiation optical system for directing the laser beam emitted by the laser source to the affected part;
    a variable magnification lens arranged movably on an optical axis of the irradiation optical system;
    first input means for inputting data concerning magnification of a contact lens to be used for treatment;
    second input means for inputting a spot size of the laser beam in air based on a movement quantity or a position of the magnification lens;
    calculation means for obtaining a real spot size of the laser beam on the affected part based on the data inputted by the first input means and the second input means; and
    spot size display means for displaying the real spot size of the laser beam obtained by the calculation means.

2. The laser treatment apparatus according to claim 1, wherein the second input means includes detecting means for detecting the movement quantity or the position of the magnification lens and inputting the detected movement quantity or the detected position to the calculation means.

3. The laser treatment apparatus according to claim 1, wherein the second input means includes an input switch or an input knob for inputting the lens movement quantity or the position of the magnification lens to the calculation means.

4. The laser treatment apparatus according to claim 1 further comprising:
    a disease case data memory capable of storing a plurality of types of disease cases to be treated and data concerning irradiation conditions corresponding to each disease case type, the data concerning irradiation conditions including at least one of data on irradiation power, irradiation time, and a spot-size of the laser beam;
    disease case selecting means for selecting a disease case type to be treated from among the disease case types stored in the disease case data memory; and
    irradiation condition display means for displaying data concerning irradiation condition corresponding to the selected disease case type.

5. The laser treatment apparatus according to claim 1 further comprising:
    a disease case data memory capable of storing a plurality of types of disease cases to be treated and data concerning irradiation conditions corresponding to each disease case type, wherein the data concerning irradiation conditions including at least one of data on irradiation power, irradiation time, and a spot size of the laser beam;
    disease case selecting means for selecting a disease case type to be treated from among the disease case types stored in the disease case data memory; and
    irradiation control means for controlling laser irradiation based on data concerning the irradiation condition corresponding to the selected disease case type.

6. A laser treatment apparatus for irradiating an affected part with a treatment laser beam, the apparatus comprising:
    a laser source for emitting the treatment laser beam;
    an irradiation optical system for directing the laser beam emitted by the laser source to the affected part;
    a variable magnification lens arranged movably on an optical axis of the irradiation optical system;
    first input means for inputting data concerning magnification of a contact lens to be used for treatment, the first input means including:
        a contact lens data memory capable of storing a plurality of types of contact lenses to be used for treatment and data concerning magnifications of each contact lens type; and
        contact lens selecting means for selecting a desired contact lens type from among the contact lens types stored in the contact lens data memory;
    wherein data concerning magnification of the selected contact lens type is read out and is inputted,
    second input means for inputting a spot size of the laser beam in air based on a movement quantity or a position of the magnification lens;
    calculation means for obtaining a real spot size of the laser beam on the affected part based on the data inputted by the first input means and the second input means; and
    spot size display means for displaying the real spot size of the laser beam obtained by the calculation means.

7. The laser treatment apparatus according to claim 6 further comprising:
    a disease case data memory capable of storing a plurality of types of disease cases to be treated and data concerning irradiation conditions corresponding to each disease case type;
    disease case selecting means for selecting a disease case type to be treated from among the disease case types stored in the disease case data memory; and
    irradiation condition display means for displaying data concerning the irradiation condition corresponding to the selected disease case type.

8. The laser treatment apparatus according to claim 7, wherein the data concerning irradiation conditions includes at least one of data on irradiation power, irradiation time, and a spot size of the laser beam,
    the laser treatment apparatus further including:
    irradiation control means for controlling laser irradiation based on the data concerning the irradiation condition corresponding to the selected disease case type.

9. The laser treatment apparatus according to claim 6, wherein the second input means includes detecting means for detecting the movement quantity or the position of the magnification lens and inputting the detected movement quantity or the detected position to the calculation means.

10. The laser treatment apparatus according to claim 6, wherein the second input means includes an input switch or an input knob for inputting the movement quantity or the position of the magnification lens to the calculation means.

11. A laser treatment apparatus for irradiating an affected part with a treatment laser beam, the apparatus comprising:
    a laser source for emitting the treatment laser beam;
    an irradiation optical system for directing the laser beam emitted by the laser source to the affected part;

a variable magnification lens arranged movably on an optical axis of the irradiation optical system;

first input means for inputting data concerning magnification of a contact lens to be used for treatment, the first input means including:

a disease case data memory capable of storing a plurality of types of disease cases to be treated and data concerning irradiation conditions corresponding to each disease case type, the data concerning irradiation conditions including data on contact lens types to be used for treatment and data concerning magnifications of each contact lens type; and disease case selecting means for selecting a disease case type to be treated from among the disease case types stored in the disease case data memory;

wherein data on contact lens type and data concerning magnification of the contact lens type corresponding to the selected disease case type is read out and is inputted, second input means for inputting a spot size of the laser beam in air based on a movement quantity or a position of the magnification lens;

calculation means for obtaining a real spot size of the laser beam on the affected part based on the data inputted by the first input means and the second input means; and spot size display means for displaying the real spot size of the laser beam obtained by the calculation means.

12. The laser treatment apparatus according to claim 11, wherein the second input means includes detecting means for detecting the movement quantity or the position of the magnification lens and inputting the detected movement quantity or the detected position to the calculation means.

13. The laser treatment apparatus according to claim 11, wherein the second input means includes an input switch or an input knob for inputting the movement quantity or the position of the magnification lens to the calculation means.

* * * * *